United States Patent [19]

Immel et al.

[11] 3,966,712

[45] June 29, 1976

[54] PROCESS FOR THE PURIFICATION OF CAPROLACTAM

[75] Inventors: Otto Immel; Hans-Helmut Schwarz, both of Krefeld, Germany

[73] Assignee: Bayer Aktiengesellschaft, Leverkusen, Germany

[22] Filed: Oct. 31, 1974

[21] Appl. No.: 519,687

Related U.S. Application Data

[63] Continuation of Ser. No. 361,465, May 18, 1973, abandoned.

[30] Foreign Application Priority Data

May 19, 1972 Germany............................ 2224505

[52] U.S. Cl............................................ 260/239.3 A
[51] Int. Cl.[2]...................................... C07D 201/16
[58] Field of Search.............................. 260/239.3 A

[56] References Cited
UNITED STATES PATENTS

| 2,988,546 | 6/1961 | Lippincott et al. | 260/239.3 A |
| 3,347,852 | 10/1967 | Ishikawa et al. | 260/239.3 A |
| 3,476,744 | 11/1969 | Berther et al. | 260/239.3 A |
| 3,485,820 | 12/1969 | Hofmann et al. | 260/239.3 A |

FOREIGN PATENTS OR APPLICATIONS

| 2,023,344 | 11/1971 | Germany |
| 583,947 | 1/1947 | United Kingdom |

*Primary Examiner*—Henry R. Jiles
*Assistant Examiner*—Robert T. Bond
*Attorney, Agent, or Firm*—Plumley and Tyner

[57] ABSTRACT

Object of the invention is a process for the purification of a caprolactam obtained by catalytic rearrangement of cyclohexanone oxime in the gaseous phase comprising crystallization said caprolactam which main impurity consists of cyclohexanone oxime from dimethylformamide, dimethylacetamide, methyl formate, ethyl formate, methyl acetate, tetrahydrofuran, 1,3 dioxane, 1,4 dioxane, propanol, butanol or amyl alcohol or from a mixture of these solvents, followed by distillation.

3 Claims, No Drawings

PROCESS FOR THE PURIFICATION OF CAPROLACTAM

This application is a continuation of our case Ser. No. 361,465 filed May 18, 1973, and now abandoned.

This invention relates to a process for the purification of caprolactam which has been obtained by the catalytic rearrangement of cyclohexanone oxime in the gaseous phase.

Numerous publications deal with the purification of caprolactam since caprolactam used, for example, for the preparation of polyamides which are made up into synthetic fibres must be in a very high state of purity. Some of the known methods of purification have considerable disadvantages. Attempts have therefore been made to improve these methods of purification, either by passing the lactam solutions through ion exchangers or by adding adsorbents, such as active charcoal or calcium silicate, or by subjecting the lactam solutions to hydrogenation or even oxidation reactions. It has also been proposed to purify caprolactam by crystallisation carried out in water or in low boiling-point aliphatic hydrocarbons, which have a low dissolving power for lactam. These methods of crystallisation are in most cases not adequate for purifying lactam and must be combined with other methods of purification.

According to U.S. Pat. No. 2,813,858, purification of caprolactam can be achieved by repeated crystallisation if the lactam is treated with a substance which is itself soluble in the lactam and lowers its melting point. Numerous such substances are mentioned, e.g. water, ammonia, cyclohexane, benzene, several ketones, alcohols and chlorinated hydrocarbons, and aliphatic and aromatic hydrocarbons in general. Among these compounds, the ones preferably used are those which have a molecular weight below 50, e.g. water and ammonia.

Other solvents have been proposed in French Pat. No. 1,490,312 for purifying caprolactam which has been obtained by ammonolysis of ε-caprolactone, for example a certain selection of esters of monocarboxylic acids, a selection of aliphatic ketones and lastly, mono- and dialkylbenzene compounds which contain from 8 to 10 carbon atoms in the molecule. It is clear from this patent specification that although numerous methods of purification which can be carried out on a technical scale are available, these have been developed specifically for lactams which have been obtained by Beckmann rearrangement. Lactams which have been obtained by some other method, e.g. by hydrolysis of ω-aminocaproic acid nitrile by the Schmidt reaction or by ammonolysis of ε-caprolactone, contain other impurities according to their methods of preparation and therefore require special methods of purification. One method of purification for lactam which has been prepared by a ring closing saponification of ω-aminocaproic acid nitrile has been disclosed e.g. in German Pat. No. 924,213. A treatment with zinc in accordance with DAS No. 1,263,772 has been recommended for purifying caprolactam which has been obtained by photooximation and rearrangement of cyclohexanone oxime.

It is also known that the nature of the impurities present depends on the process employed for producing the caprolactam and that each method of caprolactam production therefore requires its own special method of lactam purification. Although it has been disclosed in DAS No. 1,155,132 that lactam which has been prepared by catalytic rearrangement has been purified by a conventional process, this process of purification is very complicated and not satisfactory. The permanganate number 350 — 510 is given as a measure of the degree of purity but it is well known that the quality of a lactam depends on numerous specific data.

Industrially, rearrangement of cyclohexanone oxime is carried out mainly in oleum or concentrated sulphuric acid. Neutralisation of the reaction mixture results in the formation of large quantities of ammonium sulphates, the complete removal of which requires considerable time and labour. Catalytic rearrangement in the gaseous phase (see DAS No. 1,055,537) therefore assumes a position of greater importance because no additional product is produced by this process.

A crude lactam obtained by the catalytic rearrangement of cyclohexanone oxime may be expected to contain the following impurities: cyclohexanone, cyclohexanol, cyclohexanone oxime, various hexenic acid nitriles, cracking products and compounds which contain boron (in cases where a boron trioxide catalyst is used).

No simple, economical process of purification has previously been available for removing these impurities.

It has now surprisingly been found that exceptionally pure lactam can be obtained from crude lactam produced by catalytic rearrangement of the corresponding oxime in the gaseous phase by a process of purification comprising recrystallisation of the lactam from certain organic solvents followed by distillation.

Apart from the by-products formed in the process of catalytic rearrangement, the caprolactam which has to be purified may also contain a certain amount of oxime due to an incomplete rearrangement reaction. The possibility of purifying a lactam which contains oxime by a simple process constitutes a particularly important advance provided by the process according to the invention, since the removal of the last traces of oxime cannot easily be achieved by distillation or extraction.

This invention therefore relates to a process for the purification of a caprolactam which has been obtained by catalytic rearrangement in the gaseous phase comprising the steps: (i) crystallisation from dimethylformamide, dimethylacetamide, methyl formate, ethyl formate, methyl acetate, tetrahydrofuran, 1,3-dioxane, 1,4-dioxane, propanol, butanol or amyl alcohol or from a mixture of these solvents; followed by (ii) distillation.

The solvent which is particularly preferred is dimethylformamide, dimethylacetamide, ethyl formate, tetrahdrofuran, 1,3-dioxane or 1,4-dioxane.

The purification action of any of the above mentioned solvents is so efficient that, after only one recrystallisation from such a solvent, a lactam which can be regarded as sufficiently pure after distillation is obtained.

The catalytic rearrangement of cyclohexanone oxime is carried out by a known process, for example, as it is described in DAS No. 1,055,537 at a temperature in the range of from 250° to 400°C.

The process of purification according to the invention will now be explained by way of example:

From 20 to 100 parts by weight of solvent are added to 100 parts by weight of crude lactam and the lactam is dissolved by heating. The solution is then slowly cooled to from 0° to 40°C with stirring so that the lactam crystallises. Alternatively, the lactam solution may be supersaturated by removing some of the solvent by evaporation. The mother liquor is removed by filtration in the usual manner and the residue is washed with solvents or lactam solution.

The temperature at which crystallisation is carried out depends on the type of crystallisation apparatus employed but is preferably in the range of from 10° to 40°C. The proportion by weight of lactam crystals to mother liquor may be in the range of from 5:1 to 1:10. The purification process does not depend on the use of any particular crystallisation apparatus and may be carried out with any of the usual cooling, vacuum or evaporation crystallisers used industrially. Distillation of the recrystallised lactam is carried out in distillation columns which contain more than 5 theoretical trays.

If the process according to the invention is carried out continuously, the first runnings obtained from the distillation process and the residue are returned to the crystallisation apparatus. The washing liquor obtained from washing the recrystallised lactam is also introduced into the crystallisation apparatus and an appropriate amount of the mother liquor is separated off and fractionally distilled to remove the impurities. The solvent obtained by this process is used again for washing the lactam crystals. The lactam fraction which is not required to have a particularly high degree of purity is returned to the crystallisation apparatus.

The degree of purity of the caprolactam obtained is determined by making the usual measurements. The Hazen colour number is defined according to ASTM D 1209. The permanganate number is the time in seconds required for 1 ml of a N/100 KMnO$_4$ solution to reduce the colour of a solution of 1 g of ε-caprolactam in 100 ml of water to that of a comparison solution which contains 2.5 g of Co(NO$_3$)$_2$6H$_2$O and 0.01 g of K$_2$Cr$_2$O$_7$ in 1 liter of water. The volatile bases are expressed in ml of N/10 sulphuric acid for 20 g of caprolactam.

These data for purity are sensitively affected by traces of foreign substances such as cyclohexanone oxime.

The process according to the invention is now described in more detail in the following examples but is not restricted to them.

EXAMPLE 1

A pale brown crude lactam obtained by catalytic rearrangement of cyclohexanone oxime and having the following composition:

98.5% of caprolactam,
0.8% of cyclohexanone oxime,
0.7% of various by-products
was purified.

The crude lactam had the following characteristics:

| | |
|---|---|
| Solidification point | approx. 65.8°C |
| Hazen colour number | above 300 |
| Volatile bases | 7.26 |
| KMnO$_4$ number | 0. |

3.38 kg of the crude lactam were dissolved in 1.22 kg of 1,4-dioxane by heating to 60°C. The resulting solution was slowly cooled to 15°C with stirring, and 2.5 kg of lactam crystallised from the solution. After filtration, the lactam crystals were carefully washed with 1.2 kg of a solution of caprolactam in 1,4-dioxane which had been saturated at room temperature. 0.3% of NaOH were then added to 1.8 kg of this partly purified lactam and the lactam was subjected to fractional distillation at 5 mm Hg, using a column with 15 practical trays. A fraction of 1.3 kg of pure lactam which had the following characteristics was obtained:

| | |
|---|---|
| Solidification point | 69.12°C |
| Hazen colour number | 5 |
| Volatile bases | 0.06 |
| KMnO$_4$ number | >40000. |

EXAMPLE 2

3.67 kg of crude lactam having the same composition as in Example 1 were dissolved in 834 g of methyl acetate by heating to 60°C. The resulting solution was slowly cooled to 35°C with stirring. 1.8 kg of ε-caprolactam crystallised. The ε-caprolactam crystals were filtered off and washed with 1.2 kg of a solution of caprolactam in methyl acetate which had been saturated at room temperature. The purified lactam was then fractionally distilled after the addition of 0.3% of NaOH as in Example 1.

This distillation yielded 1.28 kg of pure lactam which has the following characteristics:

| | |
|---|---|
| Solidification point | 69.01°C |
| Hazen colour number | 5 |
| Volatile bases | 0.06 |
| KMnO$_4$ number | >40000 |

EXAMPLE 3

Crude lactam which had been obtained by catalytic rearrangement of cyclohexanone oxime and had the same composition and characteristic data as described in Example 1 was purified as follows:

3.82 kg of the crude lactam and 780 g of isopropanol were heated to 60°C. The resulting solution was slowly cooled to 20°C with stirring and the ε-caprolactam which crystallised was filtered off. 2.76 kg of lactam were obtained. The lactam was carefully washed with 1.2 kg of a solution of caprolactam in isopropanol which had been saturated at room temperature. 2 kg of this purified lactam were fractionally distilled at 5 mm Hg after the addition of 0.3% of NaOH as in the Example 1.

This distillation yielded 1.49 kg of pure lactam which had the following characteristics:

| | |
|---|---|
| Solidification point | 69.03°C |
| Hazen colour number | 5 |
| Volatile bases | 0.08 |
| KMnO$_4$ number | >40000 |

EXAMPLE 4

3.68 kg of the same crude lactam as described in Example 1 were recrystallised from 920 g of ethyl formate. The two substances were heated together to 60°C and the resulting solution slowly cooled to 30°C with stirring. 1.9 kg of ε-caprolactam crystallised. The crystallised ε-caprolactam was filtered off and washed with 2.2 kg of a solution of caprolactam in ethyl formate which had been saturated at room temperature. The resulting caprolactam was fractionally distilled at 5 mm Hg after the addition of 0.3% of NaOH as described in Example 1. 1.2 kg of pure lactam which had the following characteristics to identify its quality were obtained:

| | |
|---|---|
| Solidification point | 69.11°C |

-continued

| | |
|---|---|
| Hazen colour number | 5 |
| Volatile bases | 0.06 |
| KMnO₄ number | >40000 |

EXAMPLE 5

3.74 kg of the same crude lactam as in Example 1 and 860 g of dimethylformamide were heated to about 60°C. The solution was then slowly cooled to 25°C with stirring and the crystallised ε-caprolactam was filtered off. This lactam (2.6 kg) was washed with 1.2 kg of a solution of caprolactam in dimethylformamide which was saturated at room temperature.

2 kg of this purified lactam were fractionally distilled at 5 mm Hg after the addition of 0.3% of NaOH as in Example 1.

This distillation yielded 1.48 kg of pure lactam which had the following characteristics:

| | |
|---|---|
| Solidification point | 69.08°C |
| Hazen colour number | 5 |
| Volatile bases | 0.06 |
| KMnO₄ number | >40000. |

EXAMPLE 6

Crude lactam which had been obtained by catalytic rearrangement of cyclohexanone oxime and had the composition and characteristics described in Example 1 was purified as follows:

3.72 kg of the crude lactam and 880 g of isobutanol were heated to about 60°C. The solution was then slowly cooled to 12°C with stirring. The ε-caprolactam which crystallised (2.55 kg) was filtered off and washed with 2 kg of a solution of caprolactam in isobutanol which was saturated at room temperature.

1.9 kg of this purified lactam were fractionally distilled at 0.5 mm Hg after the addition of 0.3% of NaOH as in Example 1.

This distillation yielded 1.4 kg of pure lactam which had the following characteristics:

| | |
|---|---|
| Solidification point | 69.14°C |
| Hazen colour number | 5 |
| Volatile bases | 0.09 |
| KMnO₄ number | >40000 |

EXAMPLE 7

Crude lactam which had been obtained by catalytic rearrangement of cyclohexanone oxime and had the following composition:
96.2% of caprolactam
3.2% of cyclohexanone oxime
0.6% of various by-products
was purified.

This crude lactam had the following characteristics:

| | |
|---|---|
| Solidification point | about 62°C |
| Hazen colour number | above 300 |
| Volatile bases | 9.10 |
| KMnO₄ number | 0. |

3.64 kg of the crude lactam and 960 g of n-amyl alcohol were heated to 60°C. The solution was then slowly cooled to 20°C with stirring. The crystallised ε-caprolactam was separated off (2.6 kg) and washed with 2 kg of a solution of caprolactam in n-amyl alcohol which was saturated at room temperature.

1.7 kg of this purified lactam were fractionally distilled after the addition of 0.3% of NaOH as in Example 1. 1.1 kg of pure lactam which had the following characteristics was obtained:

| | |
|---|---|
| Solidification point | 69.11°C |
| Hazen colour number | 5 |
| Volatile bases | 0.06 |
| KMnO₄ number | >40000 |

EXAMPLE 8

3.54 kg of a crude lactam which had the same quality as that in Example 7 and 1.06 kg of tetrahydrofuran were heated to 60°C. The solution obtained was then slowly cooled to 20°C with stirring and the ε-caprolactam which crystallised (2.4 kg) was filtered off. The recrystallised lactam was washed with 2 kg of a solution of caprolactam in tetrahydrofuran which was saturated at room temperature.

0.3% of NaOH was added to 2 kg of this lactam which was then fractionally distilled at 5 mm Hg as in Example 1.

This distillation yielded a fraction of 1.48 kg of pure lactam which had the following characteristics:

| | |
|---|---|
| Solidification point | 69.10°C |
| Hazen colour number | 5 |
| Volatile bases | 0.10 |
| KMnO₄ above | >40000 |

EXAMPLE 9

Crude lactam which had also been obtained by catalytic rearrangement of cyclohexanone oxime and which had the following composition:

99.4% caprolactam
0.1% cyclohexanone oxime
0.5% of various by-products, was purified as follows:

3.74 kg of the crude lactam and 860 g of dimethylformamide were heated to about 60°C and the solution was then slowly cooled to 20°C with stirring. The resulting crystal sludge was filtered. The crystallised ε-caprolactam (2.67 kg) was washed with 2 kg of a solution of caprolactam in dimethylformamide which was saturated at room temperature.

0.3% of NaOH was added to 2 kg of the resulting lactam which was then fractionally distilled at 5 mm Hg as in Example 1.

This distillation yielded a fraction of 1.47 kg of pure lactam which had the following characteristics:

| | |
|---|---|
| Solidification point | 69.11°C |
| Hazen colour number | 5 |
| Volatile bases | 0.09 |
| KMnO₄ number | >40000 |

EXAMPLE 10

3.54 kg of crude lactam which had the same composition as the crude lactam described in Example 9 were recrystallised from 1.06 kg of methyl formate. The mixture was heated to about 50°C. The resulting solution was slowly cooled to 20°C with stirring. The ε- caprolactam which crystallised was separated off (2.3 kg) and washed with 2 kg of ice cold methyl formate.

1.3 kg of lactam obtained in this way were fractionally distilled at 5 mm Hg after the addition of 0.3% of NaOH as in Example 1.

This distallation yielded a fraction of 812 g of pure lactam which had the following characteristics:

| | |
|---|---|
| Solidification point | 69.10°C |
| Hazen colour number | 5 |
| Volatile bases | 0.07 |
| $KMnO_4$ number | >40000 |

EXAMPLE 11

3.6 kg of the same crude lactam as described in Example 9 were added to 1 kg of dimethyl acetamide. The mixture was heated to about 60°C and the resulting solution slowly cooled to 15°C. 2.8 kg of ε-caprolactam crystallised and were filtered off and then washed with 2 kg of a saturated solution of lactam in dimethylacetamide at room temperature.

0.3% of NaOH was added to 2 kg of this purified lactam which was then fractionally distilled at 5 mm Hg as in Example 1. This distillation yielded a fraction of 1.7 kg of pure lactam which had the following characteristics:

| | |
|---|---|
| Solidification point | 69.14°C |
| Hazen colour number | 5 |
| Volatile bases | 0.07 |
| $KMnO_4$ number | >40000 |

What we claim is:

1. A process for purification of caprolactam comprising the steps of crystallization followed by distillation wherein said caprolactam has been obtained by catalytic rearrangement in the gaseous phase and contains as main impurities a member of the group consisting of cyclohexanone oxime, cyclohexanone, cyclohexanol, various hexenic acid nitriles and cracking products and said crystallisation takes place from dimethyl formamide, tetrahydrofuran, 1,4-dioxane, propanol, butanol, amylalcohol or from a mixture of these solvents.

2. A process as claimed in claim 1 comprising the steps: (i) crystallisation from dimethylformamide, dimethylacetamide, ethyl formate, tetrahxdrofuran, 1,3-dioxane or 1,4-dioxane, or from a mixture of these solvents; followed by (ii) distillation.

3. A process for purification of caprolactam comprising the steps of crystallisation followed by distillation wherein said caprolactam has been obtained by catalytic rearrangement in the gaseous phase and contains as main impurities a member of the group consisting of cyclohexanone oxime, cyclohexanone, cyclohexanol, various hexenic acid nitriles and cracking products and said crystallisation takes place from dimethyl formamide, dimethylacetamide, methyl formate, ethyl formate, methylacetate, tetrahydrofuran, 1,3-dioxane, 1,4-dioxane, propanol, butanol, amylalcohol or from a mixture of these solvents.

* * * * *